United States Patent [19]
Lakshmanan

[11] Patent Number: 6,008,232
[45] Date of Patent: *Dec. 28, 1999

[54] METHODS FOR PREVENTING HEADACHES

[75] Inventor: Mark Chandrakant Lakshmanan, Zionsville, Ind.

[73] Assignee: Eli Lilly and Company, Indianapolis, Ind.

[ * ] Notice: This patent issued on a continued prosecution application filed under 37 CFR 1.53(d), and is subject to the twenty year patent term provisions of 35 U.S.C. 154(a)(2).

[21] Appl. No.: 09/129,072

[22] Filed: Aug. 4, 1998

Related U.S. Application Data

[60] Provisional application No. 60/056,747, Aug. 20, 1997.

[51] Int. Cl.⁶ ............ A61K 31/40; A61K 31/445; A61K 31/55
[52] U.S. Cl. ............ 514/324; 514/212; 514/422
[58] Field of Search ............ 514/212, 324, 514/422

[56] References Cited

U.S. PATENT DOCUMENTS

| | | | |
|---|---|---|---|
| 4,133,814 | 1/1979 | Jones et al. | 260/326.55 |
| 4,380,635 | 4/1983 | Peters | 546/202 |
| 4,418,068 | 11/1983 | Jones | 424/267 |
| 5,075,321 | 12/1991 | Schreiber | 514/317 |
| 5,389,670 | 2/1995 | Fontana | 514/443 |
| 5,391,557 | 2/1995 | Cullinan et al. | 514/324 |
| 5,441,947 | 8/1995 | Dodge et al. | 514/179 |
| 5,462,950 | 10/1995 | Fontana | 514/324 |
| 5,482,949 | 1/1996 | Black et al. | 514/324 |
| 5,484,808 | 1/1996 | Grinnell | 514/443 |
| 5,492,927 | 2/1996 | Gitter et al. | 514/443 |
| 5,504,094 | 4/1996 | Bruns, Jr. et al. | 514/324 |
| 5,521,198 | 5/1996 | Zuckerman | 514/324 |
| 5,534,526 | 7/1996 | Cullinan | 514/324 |
| 5,545,641 | 8/1996 | Bruns, Jr. et al. | 514/317 |
| 5,670,523 | 9/1997 | Brandi et al. | 514/324 |

FOREIGN PATENT DOCUMENTS

| | | |
|---|---|---|
| 0 747376 | 5/1996 | European Pat. Off. . |
| WO93/10113 | 5/1993 | WIPO . |
| WO93/1074 | 6/1993 | WIPO . |
| WO96/12490 | 5/1996 | WIPO . |
| WO96/40134 | 12/1996 | WIPO . |

OTHER PUBLICATIONS

Draper et al., "Effects of Raloxifene (LY139481 HCl) on Biochemical Markers of Bone and Lipid Metabolism Healthy Postmemopausal Women", Hong Kong, Fourth Int'l Symp. on Osteoporosis, Mar. 29, 1993.

Evans et al., "Raloxifene is a Tissue Specific Estrogen Agonist", Am Soc. Bone & Min. Res., Tampa, Sep. 18–22, 1993.

Frolik et al., "In Vivo and In Vitro Metabolism of Raloxifene", Am. Soc. Bone & Min. Res., Tampa Sep. 18–22, 1993.

Glasebrook et al., "Multiple Binding Sites for the Antiestrogen Raloxifene", Am Soc. Bone & Min. Res., Tampa, Sep. 18–22, 1993.

Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.

Sato et al., "DEXA Analysis of Raloxifene Effects on the Bones From Ovariectomized Rats", Am. Soc. for Bone and Min. Res., Tampa, Sep. 18–22, 1993.

Yang et al., "Raloxifene and Anti–Estrogen, Simulates the Effects of Estrogen in Inhibiting Bone Resorption Through Regulating TCGB–3 Expression in Bone;" Am Soc. for Bone and Min. Res., Tampa, Sep. 18–22, 1993.

Black et al., "Distinct, Structure–Related Profiles of Estrogenic and Anti–Estrogenic Activity in the Tamoxifen and LY117018 Series;" The Endocrine Society, Abstract 1982.

Black et al., "Uterine Bioassay of Tamoxifen, Trioxifene, and New Estrogen Antagonist (LY117018) in Rats and Mice," Life Sciences, 26:1980, 1453–1458.

Black et al., "Differential Interaction of Antiestrogens with Cytosol Estrogen Receptors," Molecular and Cellular Endocrinology, 22:1981, 95–103.

Black et al., "Evidence for Biological Action of the Antiestrogens LY117018 and Tamoxifen by Different Mechanisms," Endocrinology 109; 1981, 987–989.

Black, L.J. "Biological Actions and Binding Properites of a New Estrogen Antagonist LY117018," In: Hormone Antagosists, 129–82, 1982, (M.K. Agarwal ed.) Walter de Gruyter and Co., Berlin New York.

(List continued on next page.)

*Primary Examiner*—Phyllis G. Spivack
*Attorney, Agent, or Firm*—William R. Boudreaux; James J. Sales

[57] ABSTRACT

A method of preventing headache in a human is disclosed which comprises the administration to a human in need thereof of an effective amount of a compound of formula I wherein $R^1$ and $R^3$ are, independently, —H, —CH$_3$, —CO(C$_1$–C$_6$ alkyl), or —COAr, where Ar is optionally substituted phenyl;

$R^2$ is selected from the group consisting of pyrrolidine, piperidine, and hexamethyleneimino; or a pharmaceutically acceptable salt or solvate thereof.

4 Claims, No Drawings

OTHER PUBLICATIONS

Black, et al., LY156758: A Unique Antiestrogen Displaying High Affinity Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New Benzothiophene Derived Antiestrogen, Life Sciences, 32:1983, 1031–1036.

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Jones et al., Synthesis and Antiestrogenic Activity of [3,4–Dihydro–2 (4–methoxyphenyl–1–naphthalenyl] [4–[2–pyrrolidinyl) ethoxyl]–phenyl] methanone, methanesulfonic acid salt, Journal of Medicinal Chemistry 22:1979, 962–966.

Jones et al., Antiestrogens 2, Structure Activity Studies in a Series of 3–Aroyl–2–arylbenzo[b]thiophene Derivatives Leading to [6–Hydroxy–2–(4–hydroxyphenyl)benzo[b]thien–3–yl] [4–[2–(1–piperidinyl)ethoxy]–phenyl]methanone Hydrochloride (LY156758), a Remarkably Effective Estrogen Antagonist with Only Minimal Intrinsic Estrogenicity, J. Med.Chem. 27(8), 1984, 1057–166.

Dodge et al., Abstract to EP 747376A1, 1996.

Bryant, et al., Raloxifene (LY139481 HCl): Bone, Lipid And Uterine Effects in the Ovariectomized Rat Model *J. Bone & Min. Res.*, vol. 8, Supp. 1, No. 26, (1993).

Black, et al., "Raloxifene (LY139481 HCl) Prevents Bone Loss and Reduces Serum Cholesterol Without Causing Uterine Hypertrophy in Ovariectomized Rates". *J. Clin. Invest.*, vol. 93, 63–69 (1994).

METHODS FOR PREVENTING HEADACHES

This application claims the benefit of U.S. Provisional Application 60/056,747, filed Aug. 20, 1997.

FIELD OF THE INVENTION

The current invention provides methods for the inhibition of headaches in humans, particularly post-menopausal women.

BACKGROUND OF THE INVENTION

Headaches have been a common malady in humans throughout history, and today still remain a major problem and source of suffering and economic loss. Many hundreds of millions of dollars are spent each year on the treatment of headaches, and yet many people are often prevented from normal daily activities due to this malady.

The malady known as headache is an amorphous disease. Its symptoms are often described by the patient in very idiosyncratic terms. Descriptions of headaches by patients include terms such as "stabbing", "burning", "throbbing", etc.; and yet, what a headache is is generally understood by everyone. Its occurrence is also heavily dependent on the particular circumstances of the patient, in some cases headaches occur in relation to stress (either physical or psychological), while in other cases they are related to environmental factors or physical activities. Headaches may occur randomly or in repetitive patterns, such as the case with migraine headaches.

The epidemiological causes of headache are highly varied, ranging from relatively minor factors, such as eye strain or neck muscle strain, to very serious pathologies, such as stroke, tumor growth, and the like. However, regardless of causative mechanism, the presenting symptom to the attending physician is often simply the complaint of headache.

Treatment of headache symptoms are as varied as the causative events. Amelioration of headache symptoms may involve the treatment initiating conditions which may seem apparently distant to the presenting complaint, (treatment of hypertension or various cancerous tumors, change of eye glasses, performing special exercises, and the like). However, the most common treatment is the palliative use of analgesics, which include aspirin, non-steroidal anti-inflammatory agents (ibuprofen, acetaminophen, etc.), opiates, ergot derivatives, and corticosteroids.

Prevention of headache is likewise an area of varied regimens, including the treatment of underlying pathologies as mentioned, supra, and changes in life-styles or stress levels. However, in cases where there are no specific initiating events, prevention of headaches with pharmacologic agents is not a common medical practice. The primary reason is that agents used to treat headaches are not usually used to prevent them, and this is due to the detrimental side-effects of those agents, e.g., the gastro-intestinal toxicity of aspirin or ibuprofen, the addictive potential of the opiates, etc. For further information, see: "Harrison's Principles of Internal Medicine", Ed. Isselbacher, K. J., et al., 9th Ed., McGraw-Hill Book Co., NYC, Chp.4, pp.18–28 (1980) and references therein.

It would be of great value to medical practice, if a pharmacologic agent were available which would prevent headache without the detrimental side-effects seen with the current headache treatment drugs.

SUMMARY OF THE INVENTION

The current invention provides methods for preventing headaches in a human, which comprises the administration to a human in need thereof an effective amount of a compound of formula I

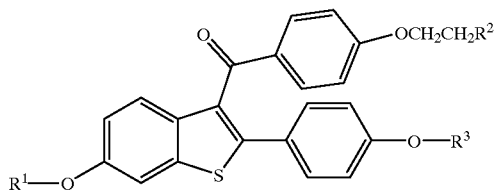

wherein $R^1$ and $R^3$ are, independently, —H, —$CH_3$, —CO ($C_1$–$C_6$ alkyl), or —COAr, where Ar is optionally substituted phenyl;

$R^2$ is selected from the group consisting of pyrrolidine, piperidine, and hexamethyleneimino; or a pharmaceutically acceptable salt or solvate, thereof.

DETAILED DESCRIPTION OF THE INVENTION

The current invention is related to the discovery that a select group of 2-aryl benzo[b]thiophenes (the compounds of formula I) are useful for preventing headaches.

General terms used in the description of compounds herein described bear their usual meanings. For example, "$C_1$–$C_6$ alkyl" refers to straight or branched aliphatic chains of 1 to 6 carbon atoms including methyl, ethyl, propyl, iso-propyl, n-butyl, pentyl, hexyl and the like.

The term "substituted phenyl" refers to a phenyl group alone or having one or more substituents selected from the group consisting of $C_1$–$C_4$ alkyl, $C_1$–$C_4$ alkoxy, hydroxy, nitro, chloro, fluoro, or tri(chloro or fluoro)methyl. "$OC_1$–$C_4$ alkyl" refers a $C_1$–$C_4$ alkyl group attached through an oxygen bridge such as, methoxy, ethoxy, n-propoxy, iso-propoxy, and the like.

The term "pharmaceutically acceptable salt" refers to either acid or base addition salts which are known to be non-toxic and are commonly used in the pharmaceutical literature. Commonly used acid addition salts are inorganic salts formed by the addition of sulfuric acid, nitric acid, hydrochloric acid, hydrobromic acid phosphoric acid, phosphorous acid and the like; or organic salts formed by the addition of acetic acid, formic acid, benzoic acid, citric acid, methanesulfonic acid and the like. Commonly used basic addition salts are the salts formed by alkali or alkaline earth hydroxides, ammonium hydroxide, alkyl or aromatic amines and the like. A preferred salt of this invention is the hydrochloride salt.

The term "solvate" refers to a molecular complex of a compound of formula I with one or more solvent molecules. Such solvent molecules would be those commonly used in the pharmaceutical literature, which are known to be innocuous to the recipient, e.g., water, ethanol, and the like.

The compounds of this invention are derivatives of centrally located carbon, i.e., the "—CO—" moiety in formula I, thus derivatives are methanones, e.g., a compound of A—CO—B, would be named [A] [B ]methanone. Further the compounds of formula I are derivatives of benzo[b] thiophene which is named and numbered according to the Ring Index, The American Chemical Society, as follows:

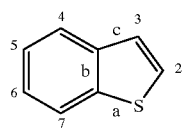

Thus, raloxifene hydrochloride, which is a preferred embodiment of this invention, is a compound of formula I, where $R^1$ and $R^3$ are both hydrogen and $R^2$ is a piperidinyl ring, the hydrochloride salt thereof. Raloxifene hydrochloride is named [2-(4-hydroxyphenyl)-6-hydroxybenzo[b]thie-3-yl][4-[2-(1-piperidenyl) ethoxy]phenyl] methanone hydrochloride.

All of the compounds used in the methods and formulations of the current invention can be made according to procedures, such as those detailed in U.S. Pat. No. 4,133,814 and U.S. Pat. No. 4,418,068, each of which is included by reference, herein. In general, the process starts with a benzo[b]thiophene having a 6-hydroxyl group and a 2-(4-hydroxylphenyl) group. The starting compound is protected, alkylated, and de-protected to form the compounds of formula I. The formula I compounds which are carboxylic esters may be prepared by methods described in U.S. Pat. No. 5,393,763, which included by reference, herein.

The compounds of formula I are members of a group of compounds previously known as antiestrogens, but which have selective estrogenic agonist and antagonist pharmacologic activities. For example, formula I compounds act as estrogen agonists in treating pathologic sequelae caused by the cessation of menses in females (see: Draper et al., "Effects of Raloxifene (LY139481 HCl ) on Biochemical Markers of Bone and Lipid Metabolism in Healthy Post-menopausal Women", Hong Kong, Fourth Int'l. Symp. on Osteoporosis, Mar. 29, 1993; U.S. Pat. Nos. 5,393,763, 5,464,845, and 5,391,557). In addition, the compounds of formula I have been shown to inhibit angiogensis, see: U.S. Pat. No. 5,610,166, which is incorporated herein by reference.

As used herein, the term "effective amount" means an amount of compound of the present invention which is capable of preventing headaches in a human, and preferably a post-menopausal women.

By "pharmaceutically acceptable formulation" it is meant that the carrier, diluent, solvent, excipients and salt must be compatible with the active ingredient (a compound of formula I) of the formulation, and not be deleterious to the recipient thereof.

Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonire; and lubricants such as talc, calcium and magnesium stearate and solid polyethyl glycols. Final pharmaceutical forms may be pills, tablets, powders, lozenges, syrups, aerosols, saches, cachets, elixirs, suspensions, emulsions, ointments, suppositories, sterile injectable solutions, or sterile packaged powders, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound of formula I required to prevent headaches according to this invention will depend upon the particular symptom and severity. Such considerations as a dosage, route of administration, and frequency of dosing are best decided by the attending physician. Generally, accepted and effective doses for oral or parenteral administration will be from 10 mg to 800 mg, and more typically between 20 mg and 100 mg. A particularly preferred dose is 60 mg/day via the oral route, especially in a post-menopausal female. Such dosages will be administered to a patient in need of treatment from once to three times each day or as often as needed to effectively control the symptoms of headache.

The formulations which follow are given for purposes of illustration and are not intended to be limiting in any way. The total active ingredients in such formulations comprises from 0.1% to 99.9% by weight of the formulation. The term, "active ingredient" means a compound of formula I, preferably Raloxifene hydrochloride.

| Ingredient | Quantity (mg/capsule) |
| --- | --- |
| Active Ingredient | 50–600 |
| Starch NF | 0–500 |
| Starch flowable powder | 0–500 |
| Silicone fluid 350 centistrokes | 0–15 |

The ingredients are blended, passed through a No. 45 mesh U.S. sieve, and filled into hard gelatin capsules.

| Ingredient | Quantity (mg/tablet) |
| --- | --- |
| Active Ingredient | 50–600 |
| Starch | 10–50 |
| Cellulose, microcrystalline | 10–20 |
| polyvinylpyrrolidone (as 10% solution in water) | 5 |
| Sodium carboxymethyl cellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50–60° C. and passed through a No. 18 mesh U.S. sieve. The sodium carboxymethyl cellulose, magnesium stearate, and talc, previously passed through a No. 60 mesh U.S. sieve, are added to the above granules and thoroughly mixed. The resultant material is compressed in a tablet forming machine to yield the tablets.

| Ingredient | Weight % |
| --- | --- |
| Active Ingredient | 0.50 |
| Ethanol | 29.50 |
| Propellant 22 (Chlorodifluoromethane) | 70.00 |
| Total | 100.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Suspension

Suspensions each containing 100 mg of a compound of formula I per 5 ml dose.

| Ingredient | Weight |
| --- | --- |
| Active Ingredient | 100 mg |
| Sodium carboxymethyl cellulose | 50 mg |
| Syrup | 1.25 mL |
| Benzoic acid solution (0.1 M) | 0.10 mL |
| Flavor | q.v. |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the entire mixture to the required volume.

Assay

Selected were 1,165 healthy, post-menopausal women. These patients were randomized between a control group 584 and a test group 581. Patients in the control group received a daily oral placebo, while the test received a 60 mg tablet of Raloxifene hydrochloride (a compound of formula I) once a day. The duration of the clinical trial was two years.

As a portion of the patient's overall evaluation, various clinical tests and parameters were measured at intervals. Also, inquiries were made of each patient as to any general symptoms or conditions they had experienced during the clinical investigation.

One of the points of inquiry for each patient was related to the suffering from headaches. Surprisingly, only 10.5% of the patients on the 60 mg dose of Raloxifene hydrochloride reported suffering from headache, whereas 15.9% of the placebo treated patients complained of headaches. This difference was statistically significant (P=0.006).

We claim:

1. A method for preventing headache in a human which comprises the administration to a human in need thereof an effective amount of a compound of formula I

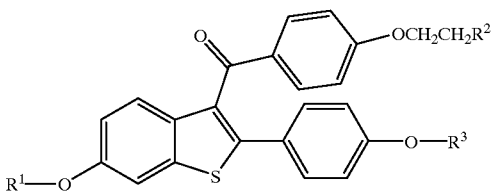

wherein $R^1$ and $R^3$ are, independently, —H, —CH$_3$, —CO(C$_1$–C$_6$ alkyl), or —COAr, where Ar is optionally substituted phenyl;

R$_2$ is selected from the group consisting of pyrrolidine, piperidine, and hexamethyleneimino; or a pharmaceutically acceptable salt or solvate thereof; with the proviso that said human is not a pre-menopausal or peri-menopausal female.

2. A method according to claim 1 wherein said compound is [2-(4-hydroxyphenyl)-6-hydroxybenzo[b]thien-3-yl][4-[2-(1-piperidinyl)ethoxy]phenyl]methanone hydrochloride.

3. A method of claim 1 wherein said human is a post-menopausal women.

4. A method according to claim 3 wherein compound is administered in an amount of 60 mg/day via the oral route.

* * * * *